(12) United States Patent
Dray

(10) Patent No.: US 6,407,084 B2
(45) Date of Patent: *Jun. 18, 2002

(54) COSMETIC OR DERMATOLOGICAL USE OF 7-HYDROXYLATED STEROIDS

(75) Inventor: Fernand Dray, Paris (FR)

(73) Assignee: Vitasterol Sarl, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/380,870

(22) PCT Filed: Mar. 6, 1998

(86) PCT No.: PCT/FR98/00457

§ 371 (c)(1),
(2), (4) Date: Oct. 15, 1999

(87) PCT Pub. No.: WO98/40074

PCT Pub. Date: Sep. 17, 1998

(30) Foreign Application Priority Data

Mar. 10, 1997 (FR) .............................. 97 02811

(51) Int. Cl.[7] .............................. A61K 31/56
(52) U.S. Cl. ................ 514/178; 514/182; 514/844
(58) Field of Search ................ 514/182, 844, 514/178

(56) References Cited

U.S. PATENT DOCUMENTS

| | | | | |
|---|---|---|---|---|
| 4,185,099 A | * | 1/1980 | Sorbini .................. | 424/238 |
| 4,681,876 A | * | 7/1987 | Marples et al. .......... | 514/182 |
| 5,461,042 A | * | 10/1995 | Loria .................... | 514/182 |
| 6,184,215 B1 | * | 2/2001 | Elias et al. ............. | 514/182 |

FOREIGN PATENT DOCUMENTS

| | | |
|---|---|---|
| EP | 0 189 738 | 8/1986 |
| EP | 0 415 766 | 3/1991 |
| EP | 0 723 775 | 7/1996 |
| WO | WO94 08588 | 4/1994 |
| WO | WO95 10283 | 4/1995 |

* cited by examiner

Primary Examiner—Barbara P. Badio
(74) Attorney, Agent, or Firm—Alston & Bird LLP

(57) ABSTRACT

A method of treating the cutaneous aging and/or the effects of UV irradiation on the skin, said method comprising applying to the skin a composition comprising at least one compound corresponding to the formula

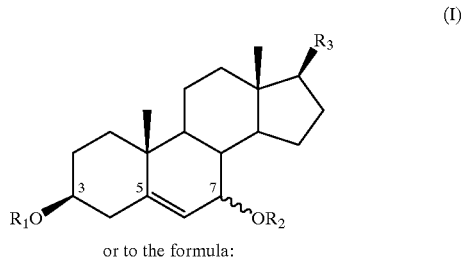

or to the formula:

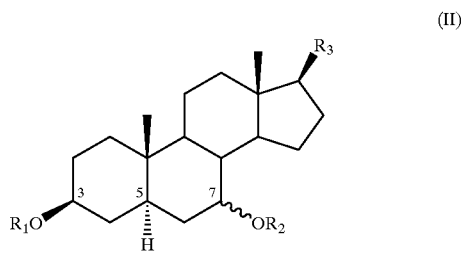

wherein R groups are as defined by the specification.

14 Claims, No Drawings

COSMETIC OR DERMATOLOGICAL USE OF 7-HYDROXYLATED STEROIDS

The present invention relates to the use of 7-hydroxylated steroids for the preparation of cosmetic or dermatological compositions for preventing and/or treating the cutaneous effects of aging and of the action of ultraviolet irradiation.

The formation of steroid hormones, their interrelations and their functions have been widely described in the prior art. The functions of pregnenolone (PREG) and of dehydroepiandrosterone (DHEA) as well as of certain of their derivatives are especially mentioned in the PCT patent application published under the number WO 94/08588.

DHEA and its sulfate derivative (S-DHEA) circulate in a significant quantity in adult men, but its level decreases with age (Orentreich et al., *J. Clin. Endocr. Metab.* 59: 551–555, 1984). It was thus proposed, for example in the French patent application published under the number 2 729 854 or the corresponding European patent application published under the number 723 775, to use S-DHEA in a cosmetic composition for topical application which is intended for the treatment of certain signs of aging. Multiple effects of DHEA have been described, but some of them oppose the processes and the pathologies associated with aging (Watson et al., *Drug & Aging* 9: 274–291, 1996).

Despite numerous experiments, it has not been possible to prove any of the explanations advanced for the effects of DHEA (Kalimi et al., *Molec. Cell. Biochem.* 131: 99–104, 1994), and the therapeutic use of DHEA has revealed undesirable secondary effects, in particular in women, as a potential precursor of androgenic hormones.

It has now been shown that the 7-hydroxylated derivatives of PREG and of DHEA are formed by an enzymatic system present in numerous tissues and organs, including the skin, where they favor the mechanisms connected with immunity (Morfin & Courchay, *J. Steroid Biochem. Molec. Biol.* 50: 91–100, 1994). Like the levels of circulating DHEA, the activity of these hydroxylating enzymes decreases with age (Doostzadeh & Morfin, *Steroids* 61: 613–620, 1996).

The Applicant is therefore interested in the effects of 7-hydroxylated steroids and their derivatives on cells which form the human skin and which are affected during aging or after UV irradiation. The research work carried out by the Applicant has allowed it to be demonstrated that the effects of glucocorticoids leading to cell apoptosis are cancelled out by the 7-hydroxylated steroids and that their action on the cutaneous cells is manifested by beneficial and protective effects.

Surprisingly, the results obtained with the compounds of the invention do not correspond to those conventionally expected with steroid hormones. Indeed, the hydroxylation process carried out by the body on PREG or DHEA is irreversible, and therefore the conventional steroid hormones cannot be produced from 7-hydroxylated derivatives.

Consequently, the use of 7-hydroxysteroids for cosmetological purposes for treating or preventing the cutaneous effects of aging has outstanding advantages with respect to the steroids of the cosmetic compositions of the prior art.

The recent work concerning the cutaneous modifications caused by age or UV and their medical treatment specifically envisages retinoic acid, α-hydroxy acids and DHEA, but does not mention 7-hydroxysteroids (Gilchrest, *Brit. J. Dermatol.* 135: 867–875, 1996; Watson et al., *Drugs & Aging* 9: 274–291, 1996).

The production of 7-hydroxylated derivatives of DHEA has been known for a long time in the tissues of the human fetus (Sulcova et al., *Endocr. Experiment.* 2: 167–172, 1968), and in the amniotic epithelium (Sulcova et al., *J. Steroid Biochem.* 7: 101–104, 1976), the human liver (Starka, *Sond. Zeit. Natur.* 17: 1–2, 1965), human testicles and epididymis (Sulcova & Starka, *Experimentia* 28: 1361–1362, 1972) and in human pre-adipocytes (Khalil et al. *J. Steroid Biochem. Molec. Biol.* 46: 585–594, 1993). In addition, the circulating levels of 7α-hydroxy-DHEA have been measured in premenopausal women at 200–300 pg/ml (Skinner et al. *Steroids* 30: 315–330, 1977), and 3β, 7α-dihydroxy-5α-androstan-17-one (7α-dihydroxyisoandrosterone) has been characterized in human urine (Jacolot et al. *J. Steroid Biochem.* 14: 663–669, 1981). More recently, the phenomenon of 7-hydroxylation has been extended to other steroids which have, in common with DHEA, a 3β-hydroxylated structure. These are PREG (Akwa et al. *Biochem. J.* 288: 959–964, 1992; Morfin & Courchay *J. Steroid Biochem. Molec. Biol.* 50: 91–100, 1994), 5α-androstane-3β, 17β-diol (Morfin et al. *Biochimie.* 59: 637–644, 1977; Morfin et al. *J. Steroid Biochem.* 12: 629–632, 1980), 3β-hydroxy-5α-androstan-17-one (Akwa et al. *Biochem. J.* 288: 959–964, 1992) and 3β-hydroxy-5α-pregnan-20-one (Strömstedt et al. *Molec. Pharmacol.* 44: 1077–1083, 1993).

Some work on 7-hydroxylated steroids proved that they were without characteristic hormonal effects of both androgenic and estrogenic type or on the secretion of pituitary hormones (Celotti et al. *J. Steroid Biochem.* 18: 397–401, 1983; Sunde et al. *J. Steroid Biochem.* 16: 483–488, 1982). All of these results therefore lead to the 7-hydroxylation of steroids being considered as a terminal process of hormonal inactivation leading to the urinary and biliary excretion of the 7-hydroxylated steroids produced (Ofner et al. *J. Steroid Biochem.* 11: 1367–1379, 1979; Strömstedt et al. *Molec. Pharmacol.* 44: 1077–1083, 1993; Khalil et al. *J. Steroid Biochem. Molec. Biol.* 48: 545–552, 1994). It is only very recently that it has been possible in part to explain the multiple effects noted with DHEA (Watson et al. *Drug & Aging* 9: 274–291, 1996) by the immunostimulatory properties of its 7-hydroxylated derivatives (Morfin & Courchay *J. Steroid Biochem. Molec. Biol.* 50: 91–100, 1994; Padgett & Loria *J. Immunol.* 153: 1544–1552, 1994; Loria et al. *J. Endocrinol.* 150: S209–220, 1996). The antiglucocorticoid properties shown by 7α- and 7β-hydroxy-DHEA have been proved and extended to other 7-hydroxylated steroids like those described in the PCT patent applications published under the numbers WO 93/20687 and WO 94/08588 for their role in the triggering of immune processes.

It therefore appears that DHEA and the production of its 7-hydroxylated derivatives decrease with age although that of the glucocorticoids does not vary. In the course of aging, the contribution of hormonal steroids to the cutaneous level is therefore found to be modified with a predominance of glucocorticoids whose promoter effects on cutaneous aging are known.

Consequently, a localized contribution of 7-hydroxylated steroids endowed with a particular but natural antiglucocorticoid effect allows the treated skin to be restored to its youthful steroid context.

However, these properties have never been described or suggested in the prior art. Thus, the PCT patent application published under the number WO 94/08588 does not describe or teach any cosmetic or dermatological application of steroid hormone derivatives. In addition, this patent application is directed at steroidal derivatives in which the substitutions in positions 3 and 7 indicated in the formula (I) below are either hydroxyls or ester functions of 1 to 10 carbon atoms.

The European patent application published under the number 415 766 describes the use of retinoid agents for combating cutaneous atrophy by an antiglucocorticoid mechanism. However, no structural relationship exists between the retinoids (vitamin A and its derivatives) and the steroids.

The European patent application published under the number 189 738 describes the use of dehydroepiandrosterone (DHEA) and of its ester derivatives for treating drying out of the skin, but these compounds are different from the steroids which are the subject of the present invention.

The European patent application published under the number 723 775 envisages the use of the sulfate of DHEA in cosmetic and dermatological compositions and suggests the addition to these compositions of steroid hormones other than the sulfate of DHEA, such as androgens, estrogens and progestagens. However, as indicated above, these steroids are without hormonal action, and their use only has the aim of alleviating the undesirable hormonal effects of DHEA and of the sulfate of DHEA. In addition, the sulfate of DHEA has no structural relationship with the steroids which are the subject of the present invention.

The invention therefore relates to the use, in a cosmetic or dermatological composition for topical application intended to prevent or treat the symptoms of cutaneous aging and/or the effects of UV irradiation on the skin, of a 7α- or 7β-substituted compound of DHEA or of PREG, which is or is not reduced in position 5, and thus corresponding to the formula:

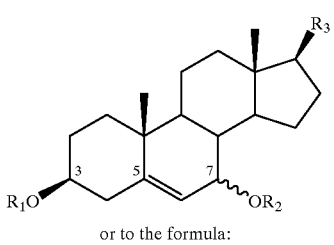

(I)

or to the formula:

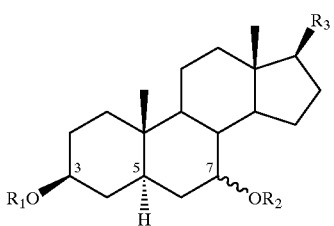

(II)

in which:

$R_1$ is selected from: a hydrogen atom, organic acid ester of 1 to 24 carbon atoms, sulfuric ester or phosphoric ester functions, or carbon-containing ether of 1 to 24 carbon atoms comprising zero or a number of nitrogen atoms, carbohydrate ethers of 3 to 100 carbon atoms and their derivatives including those comprising or not comprising one or a number of nitrogen atoms.

$R_2$ is selected from: a hydrogen atom or a fatty acid ester function of 1 to 24 carbon atoms.

$R_3$ is selected from: a hydrogen atom, an —OH group, the groups of formulae: —CO—$R_4$, —CHOH—$R_4$, =CH—$CH_3$, =COH—$CH_3$, —$CHR_4$—$CH_3$, =O, in which $R_4$ is an alkyl group comprising 1 to 10 carbon atoms, preferably methyl, which is substituted or unsubstituted.

The compounds of the invention are 7α- or 7β-substituted derivatives of DHEA or PREG and more particularly still 7α- or 7β-hydroxylated derivatives which are or are not reduced in position 5.

A preferred group of compounds of the invention are the 7α-hydroxylated derivatives, that is to say those in which the oxygen carried in position 7 is axial (7α) and the substituent $R_2$ is a hydrogen.

Another group of preferred compounds of the invention are those where $R_1$ is hydrogen, especially 7α-hydroxy-DHEA and 7α-hydroxyisoandrosterone where $R_3$ is a ketone (=O).

It is expedient to observe that the derivatives of the invention in which $R_1$ is an organic acid have an increased fat solubility which offers the advantage of improving the retention of these compounds in the cells, especially at the level of membranes, and consequently of prolonging their activity and their effect on the cutaneous cells. Among these derivatives, those are preferred in which $R_1$ is a palmitate, an oleate or a ferulate, and especially 3β-palmitoyl-7ξ-hydroxy-DHEA, 3β-oleyl-7ξ-hydroxy-DHEA and 3β-feruloyl-7ξ-hydroxy-DHEA.

The cosmetic or dermatological compositions of the invention can comprise or one or more steroid derivatives according to the invention, as well as other compounds known for their cosmetological or dermatological property, like hormones and, of course, the adjuvants or vehicles conventionally used in these fields.

For the use of a steroid derivative of the invention in a cosmetic composition intended to compensate, treat and/or prevent the cutaneous effects of aging and/or the effects of UV irradiation on the skin, said derivative is administered at a dose of between 0.05 and 10 mg per application and per day and preferably between 0.05 and 5 mg per application and per day.

The effect of restoration or of prevention of cutaneous aging in people of a certain age as well as protective effects with respect to UV is applicable for any treatment aiming to restore the cutaneous tone, tone up the skin and smooth out wrinkles.

On account of their nature, the derivatives of the invention can be employed in very diverse pharmaceutical forms for their percutaneous administration. These can be forms resulting from the addition to the derivatives of the invention of cosmetically acceptable compounds and allowing creams, pastes, gels, lotions, "water-in-oil" or "oil-in-water" emulsions as well as forms composed of liposomes of simple or mixed micelles or other penetration promoters such as lysophospholipids, cyclodextrins, polyethylene glycol, surfactants, alcohols, fatty acids and vegetable oils to be produced. This list is not limiting and any other presentation known to man can be envisaged since it is adapted to he steroid derivatives of the invention which have, as a characteristic, the property of being water-soluble and fat-soluble at the same time. Thus, the cosmetic or dermatological compositions of the invention can be present in the form of creams, lotions, gels and ointments or any other form generally used for topical applications.

Other advantages and characteristics of the invention will appear on reading the examples which follow, given in a non-limiting capacity, and showing the performances obtained by the derivatives of the invention as antiapoptotic and anti-free radical agents and promoters of the proliferation of human cutaneous cells.

EXAMPLE 1

Effects of 3β,7α-Dihydroxy-5-Androsten-17-One (7α-Hydroxy-DHEA) and of 3β,7α-Dihydroxy-5α-androstan-17-one (7α-hydroxy-ISOA) on Cell Apoptosis Induced by Glucocorticoids The thymus of C57BL/6 mice aged 4 weeks is removed. Culturing of the thymocytes is carried out for 6 hours in RPMI 1640 medium and in the presence or in the absence of the steroid tested. Apoptosis (fragmentation of the DNA) is measured by flow cytometry after labeling with propidium iodide. The apoptotic phenomenon is checked by electrophoresis of the DNA, which is visualized by ethidium bromide according to the conventional technique (observation of ranges of 200 base pairs). The results reported in Table I below were obtained:

TABLE I

| Steroids in the medium (in 10 ml of ethanol) | Apoptotic cells (%) |
| --- | --- |
| Ethanol alone | 41.5 |
| Dexamethasone $10^{-6}$ M | 72.7 |
| Dexamethasone $10^{-6}$ M + DHEA $10^{-6}$ M | 39.0 |
| Dexamethasone $10^{-6}$ M + 7α-hydroxy-DHEA $10^{-6}$ M | 58.8 |
| Dexamethasone $10^{-6}$ M + 7α-hydroxy-ISOA $10^{-6}$ M | 72.0 |
| Dexamethasone $10^{-5}$ M | 73.5 |
| Dexamethasone $10^{-5}$ M + DHEA $10^{-5}$ M | 51.4 |
| Dexamethasone $10^{-5}$ M + 7α-hydroxy-DHEA $10^{-5}$ M | 48.6 |
| Dexamethasone $10^{-5}$ M + 7α-hydroxy-ISOA $10^{-5}$ M | 46.3 |

It appears from these assays that the 7α-hydroxysteroids tested have an antiapoptotic effect opposed to that of dexamethasone on mouse T cells. Their effect at $10^{-5}$M is greater than that of their precursor steroid (DHEA or dehydroepiandrosterone or 3β-hydroxy-5-androsten-17-one).

EXAMPLE 2

Effects of 3β,7α-Dihydroxy-5-Androsten-17-One (7α-Hydroxy-DHEA) on the Viability of Human Keratinocytes in Culture Human keratinocytes are obtained from parts removed by surgery and are cultured in a monolayer to preconfluence. 7α-Hydroxy-DHEA is administered to these cultures at various concentrations in ethanolic solution (10%), each concentration being tested eight times. Controls are carried out with ethanol alone (10%). After 24 hours, the viability or the keratinocytes is measured by testing with MTT (3-(4,5-dimethylthiazol-2-yl)-2,5-diphenyltetrazolium bromide) where the mitochondrial dehydrogenase succinate transforms the MTT into blue crystals of formazan which are soluble in DMSO (Mosmann, *J. Immunol. Methods* 65: 55–63, 1983). The results of assays on the viability of the keranocytes are reported in Table II below. The cell viability is calculated according to the formula:

% viability=product $OD_{540}$×100/control $OD_{540}$.

Any value greater than 100 indicates a product favoring cell viability.

TABLE II

| Steroids in the medium (in 10% of ethanol) | Viability of keratinocytes (%) |
| --- | --- |
| 10% of ethanol alone (control) | 100 |
| 7α-hydroxy-DHEA $10^{-4}$ M | 124 ± 10 |
| 7α-hydroxy-DHEA $5.10^{-5}$ M | 111 ± 7 |
| 7α-hydroxy-DHEA $10^{-5}$ M | 119 ± 7 |
| 7α-hydroxy-DHEA $5.10^{-6}$ M | 147 ± 9 |
| 7α-hydroxy-DHEA $10^{-6}$ M | 154 ± 6 |
| 7α-hydroxy-DHEA $5.10^{-7}$ M | 139 ± 3 |
| 7α-hydroxy-DHEA $10^{-7}$ M | 147 ± 5 |
| 7α-hydroxy-DHEA $10^{-8}$ M | 127 ± 3 |

These results show that 7α-hydroxy-DHEA significantly increases the viability of human keratinocytes at concentrations of between $10^{-4}$M and $10^{-8}$M, the maximum (increases between 54% and 39% in the viability) being obtained between $5.10^{-6}$M and $10^{-7}$M. In addition, no cytotoxicity was observed. Other comparative tests demonstrated that the DHEA precursor was without effect (100±5).

EXAMPLE 3

Effects of 3β,7α-Dihydroxy-5-Androsten-17-One (7α-Hydroxy-DHEA) on the Proliferation of Human Fibroblasts in Culture The human fibroblast cultures (woman of 32 years) were inoculated into 24-well plates at a rate of 50,000 cells/well in standard culture medium (DMEM, gentamycin, amphotericin B, penicillin, L-glutamine, 10% FCS). The assays are carried out on 4 series of 3 wells. After 24 h, the fibroblasts adhere to the support and 3 series are treated with 7α-hydroxy-DHEA at concentrations of $10^{-6}$M, $5.10^{-6}$M and $10^{-7}$M. The fourth series contains only the vector (ethanol). The media are renewed daily, and at 96 h (72 h contact of the 7α-hydroxy-DHEA in the assay), the fibroblasts are counted in Malassez cells in the presence of trypan blue.

The results of the effects on the proliferation of fibroblasts are reported In Table III below.

TABLE III

| Steroids in the medium | Number of fibroblasts | Increase in the viability (%) |
| --- | --- | --- |
| Control | 190 667 ± 6 776 | / |
| 7α-hydroxy-DHEA $10^{-7}$ M | 230 667 ± 8 511 | +21 |
| 7α-hydroxy-DHEA $10^{-6}$ M | 268 000 ± 27 154 | +41 |
| 7α-hydroxy-DHEA $5.10^{-6}$ M | 258 667 ± 3 351 | +36 |

These results demonstrate that, under the experimental conditions, the treatment of fibroblasts by 7α-hydroxy-DHEA at $10^{-7}$M, $10^{-6}$M and $5.10^{-6}$M increases the cell proliferation by 21%, 41% and 36% respectively with respect to the nontreated control fibroblasts.

EXAMPLE 4

Anti-free Radical Effect of 3β,7α-Dihydroxy-5-Androsten-17-One (7α-Hydroxy-DHEA) on a Suspension of Human Keratinocytes Keratinocytes originating from a healthy donor (woman of 25 years) are cultured to the subconfluent stage in medium (KGM) which is specific for the proliferation of the keratinocytes. The suspensions obtained are divided in triplicate into 4 series of which 3 are irradiated for 30 min with a lamp emitting UVA in order to activate the production of free radicals. Among the three irradiated series, one contains the vitamins C+E (0.7%) and serves as a reference of protection, one contains 7α-hydroxy-DHEA at $10^{-6}$M and the last serves as a control. Table IV below reports the measurement of the anti-free radical effects.

The free radicals produced generate lipid peroxides which are determined by chemiluminescence (Belghmi et al. *J. Biolum. Chemilum.* 2: 113–119, 1982). The efficacy of 7α-hydroxy-DHEA is calculated on the basis of nonirradiated controls and of the reference of protection.

TABLE IV

| Keratinocytes | Chemiluminescence | Efficacy |
|---|---|---|
| Nonirradiated controls | 2 529 ± 153 | / |
| Irradiated controls | 427 750 ± 137 322 | / |
| Irradiated + 0.7% Vit. C + E | 2 970 + 238 | 100% |
| Irradiated + 7α-hydroxy-DHEA $10^{-6}$ M | 44 164 ± 13 303 | 90% |

Under the conditions of this study the in vitro anti-Free radical efficacy of 7α-hydroxy-DHEA is 90% at $10^{-6}$M. 7α-Hydroxy-DHEA can be considered as a good anti-free radical product.

What is claimed is:

1. A method of treating the cutaneous effects of aging, said method comprising applying to the skin a composition comprising at least one compound corresponding to the formula:

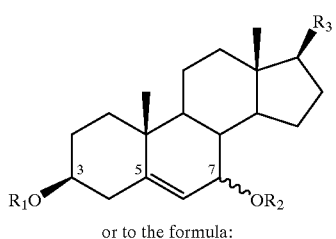

(I)

or to the formula:

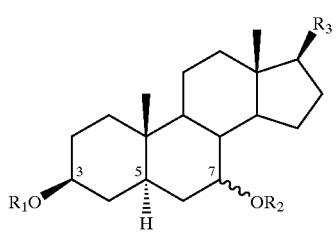

(II)

in which:

$R_1$ is selected from: a hydrogen atom, organic acid ester of 1 to 24 carbon atoms, sulfuric ester or phosphoric ester functions, or carbon-containing ether of 1 to 24 carbon atoms optionally containing one or more nitrogen atoms, carbonhydrate ethers of 3 to 100 carbon atoms optionally containing one or more nitrogen atoms;

$R_2$ is selected from: a hydrogen atom or a fatty acid ester function of 1 to 24 carbon atoms;

$R_3$ is selected from: a hydrogen atom, an —OH group, the groups of formulae: —CO—$R_4$, —CHOH—$R_4$, =Ch—$CH_3$, =COH—$CH_3$, —$CHR_4$—$CH_3$, =O, in which $R_4$ is an alkyl group -comprising 1 to 10 carbon atoms, which is substituted or unsubstituted.

2. The method of claim 1, wherein $R_2$ and/or $R_1$ is a hydrogen atom.

3. The method of claim 1, wherein $R_3$ is a ketone.

4. The method of claim 1, wherein $R_1$ is a fatty acid ester function selected from an oleate, a palmitate or a ferulate.

5. The method of claim 2, wherein the compound of formula (I) or (II) is a 7a-hydroxy-DHEA.

6. The method of claim 3, wherein the compound of formula (I) or (II) is a 7a-hydroxyisoandrosterone.

7. The method of claim 4, wherein the compound of formula (I) and (II) is selected from the group consisting of 3β-palmitoyl-7ξ-hydroxy-DHEA, 3β-oleyl-7ξ-hydroxy-DHEA and 3β-feruloyl-7ξ-hydroxy-DHEA.

8. The method of claim 1, wherein the composition contains at least one compound of formula (I) or (II) combined with one or more adjuvants or vehicles used in cosmetology or dermatology.

9. The method of claim 8, wherein the composition is in the form of a cream, lotion, gel or ointment.

10. The method of claim 1, which comprises applying to the skin a dose of said composition of between 0.05 and 10 mg per application and per day.

11. The method of claim 1, which comprises applying to the skin a dose of said composition of between 0.05 and 5 mg per application and per day.

12. The method according to claim 1, wherein the composition is a composition aiming to restore the cutaneous tone.

13. The method according to claim 1, wherein the composition is a composition aiming to tone up the skin.

14. The method according to claim 1, wherein the composition is a composition aiming to smooth out wrinkles.

* * * * *

UNITED STATES PATENT AND TRADEMARK OFFICE
CERTIFICATE OF CORRECTION

PATENT NO. : 6,407,084 B2
DATED : June 18, 2002
INVENTOR(S) : Dray

It is certified that error appears in the above-identified patent and that said Letters Patent is hereby corrected as shown below:

Column 7,
Tabke IV, line 3, under second sub-heading, "238" should read -- 288 --.

Column 8,
Line 1, "carbonhydrate" should read -- carbohydrate --;
Line 8, "Ch" should read -- CH --;
Lines 17 and 19, "7a" should read -- 7α --.

Signed and Sealed this

Nineteenth Day of November, 2002

Attest:

JAMES E. ROGAN
Attesting Officer
Director of the United States Patent and Trademark Office